United States Patent
Pequignot

(10) Patent No.: US 11,885,787 B2
(45) Date of Patent: Jan. 30, 2024

(54) METHOD AND DEVICE FOR MEASURING ATMOSPHERIC PARAMETERS TO ESTIMATE THE QUALITY OF THE AIR AND THE CLIMATE VARIABLES

(71) Applicant: Centre National d'Etudes Spatiales, Paris (FR)

(72) Inventor: Eric Pequignot, Pompertuzat (FR)

(73) Assignee: CENTRE NATIONAL D'ETUDES SPATIALES, Paris (FR)

( * ) Notice: Subject to any disclaimer, the term of this patent is extended or adjusted under 35 U.S.C. 154(b) by 430 days.

(21) Appl. No.: 17/185,353

(22) Filed: Feb. 25, 2021

(65) Prior Publication Data

US 2021/0181173 A1    Jun. 17, 2021

Related U.S. Application Data

(63) Continuation of application No. PCT/FR2019/051961, filed on Aug. 26, 2019.

(30) Foreign Application Priority Data

Aug. 27, 2018    (FR) ..................... 18/57683

(51) Int. Cl.
    *G01N 33/00*    (2006.01)
    *G01N 15/06*    (2006.01)
    (Continued)

(52) U.S. Cl.
    CPC ......... *G01N 33/0075* (2013.01); *G01N 15/06* (2013.01); *G01N 21/31* (2013.01);
    (Continued)

(58) Field of Classification Search
    CPC ......... G01N 2021/1795; G01N 1/2273; G01N 2021/1793; G01N 33/0075; G01N 15/06;
    (Continued)

(56) References Cited

U.S. PATENT DOCUMENTS

| | | | |
|---|---|---|---|
| 6,456,226 B1* | 9/2002 | Zheng ..................... | G01S 13/87 340/963 |
| 7,030,991 B1* | 4/2006 | Kampe .................. | G02B 23/00 356/450 |

(Continued)

FOREIGN PATENT DOCUMENTS

| | | |
|---|---|---|
| CN | 101419160 | 4/2009 |
| FR | 2988486 | 9/2013 |

OTHER PUBLICATIONS

International Search Report for International Application PCT/FR2019/051961, dated Nov. 12, 2019.
(Continued)

*Primary Examiner* — Mohammad K Islam
(74) *Attorney, Agent, or Firm* — Burris Law, PLLC

(57) ABSTRACT

The present disclosure relates to a method and a device for measuring at least one atmospheric parameter (gas, temperature). The method includes implementing steps of acquiring spectral images in the ultraviolet and/or the visible and/or the infrared range and scanning according to a tomographic principle. The spectral images are acquired using a network of optical systems such as infrared cameras, and are used to estimate the air quality and/or meteorological and/or climate parameters in a geographic area, for example an urban agglomeration.

12 Claims, 1 Drawing Sheet

Figure 1:
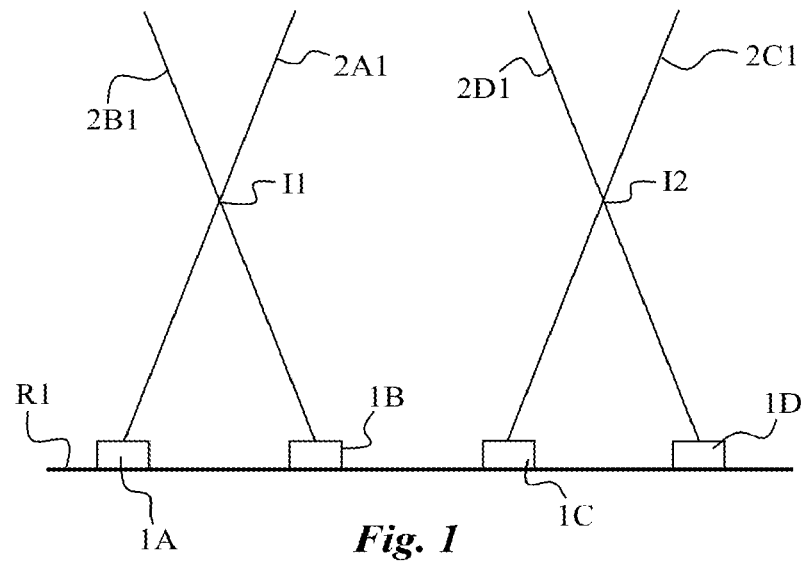

(51) Int. Cl.
*G01N 21/31* (2006.01)
*G01W 1/06* (2006.01)
*G01N 21/17* (2006.01)

(52) U.S. Cl.
CPC ....... *G01W 1/06* (2013.01); *G01N 2015/0693* (2013.01); *G01N 2021/1795* (2013.01)

(58) Field of Classification Search
CPC ........... G01N 21/31; G01N 2015/0693; G01N 33/0004; G01N 33/0009; G01N 2015/0046; G01N 2021/1787; G01K 11/125; G01W 1/00; G01W 1/06; G01W 1/04; Y02A 10/40; Y02A 90/10
See application file for complete search history.

(56) References Cited

U.S. PATENT DOCUMENTS

| | | | |
|---|---|---|---|
| 9,816,863 B1* | 11/2017 | Lietzke | G01W 1/10 |
| 9,952,146 B1* | 4/2018 | Gordley | G01N 21/3518 |
| 2002/0041328 A1* | 4/2002 | LeCompte | G01C 11/025 |
| | | | 348/144 |
| 2005/0151965 A1* | 7/2005 | Bissett, III | G01J 3/2823 |
| | | | 356/73 |
| 2006/0126959 A1* | 6/2006 | Padwick | G06V 20/13 |
| | | | 382/254 |
| 2009/0055102 A1* | 2/2009 | Laufer | G01N 21/3504 |
| | | | 702/188 |
| 2009/0262978 A1* | 10/2009 | Zavagli | G06V 10/25 |
| | | | 703/2 |
| 2010/0241361 A1* | 9/2010 | Hofvander | G01K 11/125 |
| | | | 702/24 |
| 2013/0030845 A1* | 1/2013 | Brown | G06V 20/13 |
| | | | 705/4 |
| 2013/0128271 A1* | 5/2013 | Smith | G01N 21/39 |
| | | | 356/437 |
| 2015/0233962 A1* | 8/2015 | Tchoryk | G01S 7/4808 |
| | | | 356/28 |
| 2016/0142654 A1* | 5/2016 | Vaillancourt | G02B 5/008 |
| | | | 348/164 |
| 2019/0120957 A1* | 4/2019 | Herring | H04B 7/22 |
| 2020/0278475 A1* | 9/2020 | Shao | G01W 1/11 |

OTHER PUBLICATIONS

Office Action with Search Report issued in corresponding RU Application 2021104260/28, dated Jan. 9, 2023, 6 pages.

* cited by examiner

METHOD AND DEVICE FOR MEASURING ATMOSPHERIC PARAMETERS TO ESTIMATE THE QUALITY OF THE AIR AND THE CLIMATE VARIABLES

CROSS-REFERENCE TO RELATED APPLICATIONS

This application is a continuation of International Application No. PCT/FR2019/051961, filed on Aug. 26, 2019, which claims priority to and the benefit of FR 18/57683, filed on Aug. 27, 2018. The disclosures of the above applications are incorporated herein by reference.

FIELD

The present disclosure relates to the field of measuring atmospheric parameters, in particular for the purposes of monitoring, forecasting and managing the quality of the air.

BACKGROUND

The statements in this section merely provide background information related to the present disclosure and may not constitute prior art.

Techniques allowing monitoring the quality of the air are known by measurement of pollutant concentrations in air samples collected by measuring stations. For example, the French territory is equipped with several hundred stations of this type. Such measuring stations, however, constitute expensive infrastructures and whose density is relatively low in the territory.

The air samples thus collected are generally used to estimate the air quality using digital chemistry transport models. These digital models can require significant calculation times, leading to a limitation of the studied geographical area and/or the number of measurement stations implemented in the area of interest.

In doing so, in order to estimate pollution levels at fine spatial scales, it is necessary to resort to measurement data smoothing and propagation techniques.

Such techniques can result in an underestimation of the pollution levels and more generally in an unsatisfactory quality of analyzes and forecasts to which they give rise.

SUMMARY

This section provides a general summary of the disclosure and is not a comprehensive disclosure of its full scope or all of its features.

In one form, the present disclosure provides a method and a device which are capable of improving the quality of the analysis and forecasts of air quality, while reducing the cost of infrastructure and of the implementation thereof.

The present disclosure provides, according to a first aspect, a method for measuring at least one atmospheric parameter, where the method includes an acquisition step and a scanning step as defined below.

In the acquisition step, a series of spectral images of the Earth's atmosphere are simultaneously acquired with optical systems, in particular multispectral optical systems operating in a wavelength domain from ultra-violet to infrared. For example, these optical systems can be imagers and/or radiometers and/or spectro-imagers and/or spectro-radiometers.

The term "spectral image" or "spectrometric image" means an image which may typically comprise a matrix of N*M pixels, with N≥1 and M≥1. For example, in the particular case of an image acquired using a radiometer, N and M can each be equal to 1 such that this image comprises a single pixel.

On the one hand, the optical systems which are implemented in the method according to the present disclosure are located in the Earth's atmosphere and are fixed relative to an earth frame reference.

On the other hand, the optical systems which are implemented in this method are oriented such that the spectral images that they acquire contain measurement data of said at least one atmospheric parameter along respective lines of sight of said optical systems.

On the other hand again, these optical systems are arranged such that, during the acquisition step, there is at least one point of intersection between two lines of sight, such that two spectral images which are simultaneously acquired along these two lines of sight contain mutual measurement data of the at least one atmospheric parameter, these mutual measurement data being representative of the at least one atmospheric parameter at a point of the Earth's atmosphere corresponding to said point of intersection.

According to the present disclosure, the orientation of the optical systems is changed during the scanning step, and the acquisition and scanning steps are repeated so as to acquire a succession of series of spectral images comprising a set of mutual measurement data representative of the at least one atmospheric parameter at a set of points of the Earth's atmosphere.

Such a method allows carrying out measurements of atmospheric parameters using inexpensive infrastructure and improving the quality of the analyzes and forecasts of air quality, in particular at the scale of a geographical area whose extent is relatively small such as an urban agglomeration.

By way of non-limiting examples, the at least one atmospheric parameter can be selected among atmospheric temperature and/or among at least one atmospheric gas having a signature in the ultraviolet and/or the visible and/or the infrared such as $O_3$, $NO_2$, $SO_2$, CO, PM1, PM2.5, PM10, $H_2O$, $CO_2$, $CH_4$, $N_2O$ or $NH_3$.

Indeed, the optical systems of the present disclosure allow measuring scientific parameters of interest subject to a legislation (e.g. $O_3$, $NO_2$, $SO_2$, CO; fine particles PM1, PM2.5, PM10) and/or subject to recurring pollution peaks (e.g. $O_3$, $NO_2$, PM2.5, PM10), as well as complementary products such as meteorological fields (e.g. T, $H_2O$), greenhouse gases (e.g. $CO_2$, $CH_4$, $N_2O$), fire markers for example of forest (e.g. $SO_2$, CO) or even agricultural pollutants (e.g. $NH_3$).

In one form, during the scanning step, the orientation of the optical systems can be changed such that, between the acquisition step preceding this scanning step and the acquisition step following this scanning step, said at least one point of intersection passes from a first geographic coordinate to a second geographic coordinate, this second geographic coordinate being different from said first geographic coordinate in longitude and/or in latitude and/or in elevation.

According to a second aspect, the present disclosure also concerns a method for studying at least one atmospheric parameter implementing the measurement method which is described above.

Preferably, this method for studying at least one atmospheric parameter, can further comprises a step of analyzing the acquired spectral images. Such an analysis step preferably comprises a step of inverting spectral images using at least one portion of the set of mutual measurement data contained in these spectral images.

According to a third aspect, the present disclosure also concerns a device for measuring at least one atmospheric parameter. This device comprises a network of optical systems which are arranged to implement a method for measuring at least one atmospheric parameter as described above.

As indicated above, the optical systems can be imagers and/or radiometers and/or spectro-imagers and/or spectro-radiometers. In other words, the optical systems can be infrared cameras.

The distance between two adjacent optical systems can typically be comprised between 10 m and 20 km, preferably between 2 km and 5 km, more preferably equal to 3 km.

According to a first variant, the optical systems can be fastened on respective supports which are secured to the ground, such as pylons, buildings, water towers or even tethered balloons.

Already existing infrastructures can thus be used.

According to a second variant, the optical systems can be on board one or more stationary aircraft(s), such as drones or atmospheric balloons.

According to a fourth aspect, the present disclosure also concerns a use of the methods and/or the device which are described above for estimating the quality of the air and/or meteorological and/or climatic parameters of a geographical area whose extent is preferably comprised between 100 m and 100 km. Without limitation, this geographical area can be an urban agglomeration, an industrial site, a forest or an agricultural site.

The present disclosure thus allows constituting a ground remote sensing tomographic network capable of measuring the quality of the urban air on the residential scale. This solution allows, for example, informing users or inhabitants of their individual exposure to air pollutants thanks to a reliable and continuous measurement at the local scale.

Further areas of applicability will become apparent from the description provided herein. It should be understood that the description and specific examples are intended for purposes of illustration only and are not intended to limit the scope of the present disclosure.

DRAWINGS

Figure 2:
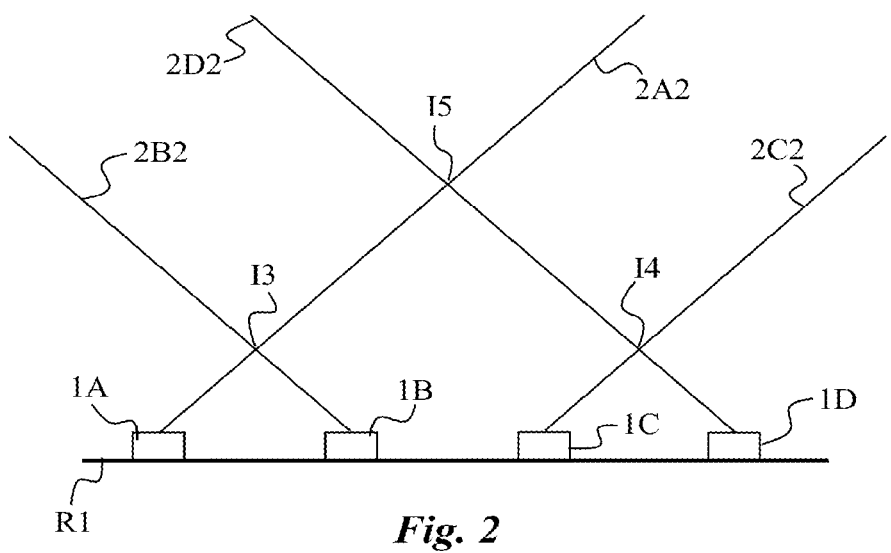

In order that the disclosure may be well understood, there will now be described various forms thereof, given by way of example, reference being made to the accompanying drawings, in which:

FIG. 1 schematically represents a network of optical systems according to the present disclosure in a first configuration; and FIG. 2 shows the network of optical systems of FIG. 1 in a second configuration.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The present disclosure concerns a device and a method for measuring at least one atmospheric parameter implementing a step of simultaneously acquiring a series of spectral images of the Earth's atmosphere using optical systems.

The atmospheric parameter(s) may for example consist of any combination of atmospheric gases having a signature in the ultraviolet and/or infrared such as $O_3$, $NO_2$, $SO_2$, $CO$, PM1, PM2.5, PM10, $H_2O$, $CO_2$, $CH_4$, $N_2O$, $NH_3$. Another example of an atmospheric parameter is atmospheric temperature.

An acquisition step is schematically illustrated in FIG. 1.

FIG. 1 shows a network of four optical systems 1A-1D. These optical systems 1A-1D are typically cameras such as imagers, radiometers, spectro-imagers, or spectro-radiometers, which are capable of acquiring spectral images in a wavelength domain from ultra-violet to infrared.

The optical systems 1A-1D are located in the Earth's atmosphere and are fixed relative to an earth frame reference R1. The term "fixed optical systems" means optical systems having a relative position relative to said earth frame reference R1 which is invariable during the implementation of the method of the present disclosure, independently of the orientation of these optical systems which can be changed during the implementation of the method of the present disclosure.

For this purpose, the optical systems 1A-1D can be mounted on respective supports which are secured to the ground, such as pylons, buildings, water towers or even tethered. Preferably, these supports have a power supply and/or internet in order power the optical systems. The device can also comprise power supply means of the solar battery type, and/or wifi connection means, for example 3G or 4G, and/or remote connection means of any other type.

Alternatively, the optical systems 1A-1D can be on board one or more stationary aircraft(s), such as drones or atmospheric balloons.

By way of a non-limiting example, the distance between two adjacent optical systems can be about 3 km. More generally, depending on the geographical area to be studied, this distance can be comprised between 10 m and 20 km. Of course, the distance between each pair of adjacent optical systems can be identical or different. In the example of FIG. 1, the distance between the optical systems 1A and 1B is identical to the distance between the optical systems 1B and 1C and to the distance between the optical systems 1C and 1D.

With reference to FIG. 1, the optical systems 1A-1D are oriented such that the spectral images they acquire contain measurement data of at least one atmospheric parameter along respective lines of sight 2A1-2D1 of said optical systems 1A-1D.

In other words, to each of the optical systems 1A-1D corresponds a respective line of sight 2A1-2D1 along which each of these optical systems 1A-1D acquires a spectral image or a series of spectral images. In particular, the optical system 1A acquires a spectral image or a series of spectral images along the line of sight 2A1, the optical system 1B acquires a spectral image or a series of spectral images along the line of sight 2B1, etc. (see FIG. 1).

During the acquisition step, in the configuration illustrated in FIG. 1, the optical systems 1A-1D are arranged such that there is at least one point of intersection between two lines of sight. In this example, there is at least one point of intersection I1 between the lines of sight 2A1 and 2B1, and a point of intersection I2 between the lines of sight 2C1 and 2D1.

Such an arrangement allows the simultaneous acquisition of two spectral images by the optical systems 1A and 1B, along the lines of sight 2A1 and 2B1. These two spectral images contain mutual measurement data of the at least one atmospheric parameter. Theses mutual measurement data are representative of the at least one atmospheric parameter at a point of the Earth's atmosphere corresponding in this case to the point of intersection I1.

Likewise, such an arrangement allows the simultaneous acquisition of two spectral images by the optical systems 1C and 1D, along the lines of sight 2C1 and 2D1. These two spectral images contain mutual measurement data of the at least one atmospheric parameter. These mutual measurement data are representative of the at least one atmospheric parameter at a point of the Earth's atmosphere corresponding in this case to the point of intersection I2.

Thus, during the acquisition step in the configuration illustrated in FIG. 1, a first series comprising two spectral images is acquired, this series of spectral images comprising a set of mutual measurement data representative of the at least one atmospheric parameter at a set of two points of the Earth's atmosphere corresponding to the points of intersection I1 and I2.

The present disclosure allows acquiring a succession of series of spectral images thanks to the implementation of a scanning step, according to a tomographic principle.

The scanning step consists in changing the orientation of the optical systems 1A-1D as illustrated by changing the orientation of the lines of sight associated with these optical systems between the configuration of FIG. 1 and the configuration of FIG. 2.

According to the present disclosure, such acquisition and scanning steps are repeated successively so as to acquire a succession of series of spectral images comprising a set of mutual measurement data representative of the at least one atmospheric parameter at a set of points of the Earth's atmosphere.

In the example of FIGS. 1 and 2, after acquiring the two spectral images in the configuration illustrated in FIG. 1 and then changing the orientation of the optical systems 1A-1D to achieve the configuration illustrated in FIG. 2, an acquisition step is carried out in the configuration of FIG. 2.

More precisely, in the configuration of FIG. 2, the optical systems 1A-1D are arranged such that there is a point of intersection I3 between the lines of sight 2A2 and 2B2, a point of intersection I4 between the lines of sight 2C2 and 2D2, and a point of intersection I5 between the lines of sight 2A2 and 2D2. The lines of sight 2A2, 2B2, 2C2 and 2D2 correspond respectively to the optical systems 1A, 1B, 1C and 1D in the configuration of FIG. 2.

In this arrangement, two spectral images can thus be simultaneously acquired along the lines of sight 2A2 and 2B2 containing mutual measurement data of the at least one atmospheric parameter. These mutual measurement data are representative of the at least one atmospheric parameter at a point of the Earth's atmosphere corresponding to the point of intersection I3.

The arrangement illustrated in FIG. 2 also allows the simultaneous acquisition of two spectral images along the lines of sight 2C2 and 2D2 containing mutual measurement data of the at least one atmospheric parameter. These mutual measurement data are representative of the at least one atmospheric parameter at a point of the Earth's atmosphere corresponding to the point of intersection I4.

In addition, in this configuration, the two spectral images acquired by the optical systems 1A and 1D, along the lines of sight 2A2 and 2D2, further contain mutual measurement data representative of the at least one atmospheric parameter at a point of the Earth's atmosphere corresponding to the point of intersection I5.

Therefore, the acquisition step, which is carried out in the configuration illustrated in FIG. 2, allows acquiring a second series of two spectral images comprising a set of mutual measurement data representative of the at least one atmospheric parameter at a set of three points of the Earth's atmosphere corresponding to the points of intersection I3, I4 and I5.

The successive repetition of such acquisition and scanning steps can be carried out such that the set of mutual measurement data is representative of the at least one atmospheric parameter at a set of points of the Earth's atmosphere which are located in a substantially horizontal plane and/or in a substantially vertical plane and/or in a volume of the Earth's atmosphere.

For this purpose, the orientation of the optical systems 1A-1D during a scanning step can be changed such that, from an acquisition step prior to this scanning step to an acquisition step subsequent to this scanning step, one or more point(s) of intersection each pass from a first geographic coordinate to a second geographic coordinate, this second geographic coordinate being different from said first geographic coordinate in longitude and/or in latitude and/or in elevation.

The density of the lines of sight and the points of intersection, that is to say the number of repetitions of the acquisition and scanning steps as well as the pitch or increment of the orientation angle of the optical systems, can be adapted depending on the topology of the area of interest, the desired horizontal and vertical resolutions, the density of the optical systems and/or the optical horizon of each spectral band or channel of each optical system.

The optical systems are preferably disposed at an elevated position, that is to say in a configuration maximizing the geometrical horizon.

In one form, the optical systems 1A-1D are mounted on robotic turrets (not represented) allowing orienting these optical systems at an angle comprised between −180° and +180° in a longitudinal direction and at an angle comprised between 0° and +90° in a latitudinal direction. The latitudinal angle is counted relative to the horizontal on the ground positively towards the zenith. Such an form allows scanning an upper half-hemisphere.

In another form, the latitudinal angle can be comprised between −90° and +90° so as to also scan a lower half-hemisphere, and thus to evaluate the possible contribution of the measurement of the surface reflectance as well as the incidence thereof in the radiative transfer (direct modeling) and in the inversion (see below).

Any type of scanning can be considered without departing from the scope of the present disclosure and the preceding examples are in no way limiting.

The present disclosure allows studying atmospheric parameters by analyzing spectral images acquired according to the principles described above.

In one form, an analysis step is implemented and includes a step of inverting the spectral images, by using at least one portion of the set of mutual measurement data contained in these spectral images.

The analysis can be carried out using a bayesian multi-line-of-sight inversion software.

In order to take into account the temporal evolution of at least one atmospheric parameter, the analysis can be carried out sequentially, by working in anomaly between time t and time t−1 h. For example, the preconceptions can be provided by the fields calculated at t−1 h for the gases and by the estimate made at t for complementary products of the meteorological field type such as T and $H_2O$. The initial preconception can be derived from an analysis or forecast carried out by meteorological centers on the studied geographical area.

A sequential temporal processing allows eliminating a portion of the evolutions of the geophysical variables (atmospheric variables or characteristics of reflective surfaces) and therefore to keep a linear direct model. It also allows considerably accelerating the calculation times.

Of course, the present disclosure is not limited to the particular examples which have just been described and those skilled in the art will be able to carry out any adaptation or to implement additional steps or features without departing from the scope of the present disclosure.

Thus, a camera calibration step can be implemented, for example using light emitters whose spectrum is well characterized (radiometric calibration) or even using black and white targets having predefined geometric patterns (geometric calibration).

Among other advantages, this present disclosure allows:
estimating the air quality with a residential spatio-temporal measurement resolution less than 250 m/h,
producing study results in real time by a direct measurement rather than by a digital model, this with an accuracy in the range of 15-25%,
completely covering an urban agglomeration with a network of measurement stations which are four hundred times denser than the existing networks,
carrying out a three-dimensional characterization of the atmosphere, and
accessing complementary products such as meteorological fields (e.g. T, $H_2O$), greenhouse gases (e.g. $CO_2$, $CH_4$, $N_2O$), fire markers for example of forest (e.g. $SO_2$, CO) or even agricultural pollutants (e.g. $NH_3$).

The fields of application of this present disclosure are numerous and comprise in particular the local and continuous monitoring of the quality of the urban air, the monitoring of industrial sites for example by targeting greenhouse gases, civil security for example by detecting forest fires, agriculture, infrared thermography of buildings, territorial development, health for example by studying the correlation between pollution and prevalence of diseases.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for measuring at least one atmospheric parameter, the method comprising:
simultaneously acquiring, as an acquisition step, a series of spectral images of Earth's atmosphere with a plurality of optical systems, wherein the plurality of optical systems are located in the Earth's atmosphere, fixed relative to an earth frame reference, oriented such that the spectral images that they acquire contain measurement data of the at least one atmospheric parameter along respective lines of sight of the optical systems, and arranged such that, during the acquisition step, there is at least one point of intersection between two lines of sight, such that two spectral images which are simultaneously acquired along the two lines of sight contain mutual measurement data of the at least one atmospheric parameter, wherein the mutual measurement data is representative of the at least one atmospheric parameter at a point of the Earth's atmosphere corresponding to the point of intersection; and
changing, as a scanning step, orientation of the optical systems, wherein the acquisition step and the scanning step are repeated so as to acquire a succession of series of spectral images comprising a set of mutual measurement data representative of the at least one atmospheric parameter at a set of points of the Earth's atmosphere.

2. The method according to claim 1, wherein the at least one atmospheric parameter is selected from atmospheric temperature, at least one atmospheric gas, or a combination thereof, wherein the at least one atmospheric gas has a signature in ultraviolet, visible, infrared or a combination thereof such as $O_3$, $NO_2$, $SO_2$, CO, PM1, PM2.5, PM10, $H_2O$, $CO_2$, $CH_4$, $N_2O$ or $NH_3$.

3. The method according to claim 1, wherein, during the scanning step, the orientation of the optical systems is changed such that, between the acquisition step preceding a respective scanning step and the acquisition step following the respective scanning step, the at least one point of intersection passes from a first geographic coordinate to a second geographic coordinate, wherein the second geographic coordinate is different from the first geographic coordinate in longitude, in latitude, in elevation, or a combination thereof.

4. The method according to claim 1 further comprising:
analyzing, as an analyzing step, the acquired spectral images, wherein the analyzing step comprises inverting the spectral images using at least one portion of the set of mutual measurement data contained in the spectral images.

5. A device for measuring at least one atmospheric parameter using the method of claim 1, the device comprising a network of optical systems.

6. The device according to claim 5, wherein a distance between two adjacent optical systems is between 10 m and 20 km, preferably between 2 km and 5 km, more preferably equal to 3 km.

7. The device according to claim 5, wherein the optical systems are fastened on respective supports which are secured to ground.

8. The device according to claim 7, wherein the ground includes a pylon, a building, a water tower, a tethered balloon, or a combination thereof.

9. The device according to claim 5, wherein the optical systems are on board one or more stationary aircrafts.

10. The device according to claim 9, wherein the one or more stationary aircrafts include a drone, an atmospheric balloon, or a combination thereof.

11. The device according to claim 5, wherein the optical systems include an imager, a radiometer, a spectro-imager, a spectro-radiometer, or a combination thereof.

12. The device according to claim 5, wherein the device comprises at least one processor.

* * * * *